United States Patent [19]

Weissman

[11] Patent Number: 4,790,754

[45] Date of Patent: Dec. 13, 1988

[54] STABILIZED DENTURE ATTACHMENT

[75] Inventor: Bernard Weissman, New York, N.Y.

[73] Assignee: Ipco Corporation, White Plains, N.Y.

[21] Appl. No.: 131,654

[22] Filed: Dec. 11, 1987

[51] Int. Cl.⁴ ............................................ A61C 13/225
[52] U.S. Cl. ...................................... 433/182; 433/181
[58] Field of Search ................. 433/181, 182, 180, 183

[56] References Cited

U.S. PATENT DOCUMENTS

| 1,765,851 | 6/1930 | Richardson | 433/182 |
| 3,117,377 | 1/1964 | Poveromo | 433/182 |
| 3,710,466 | 1/1973 | Poveromo | 433/182 |
| 4,196,516 | 4/1980 | Poveromo | 433/182 |

Primary Examiner—John J. Wilson
Attorney, Agent, or Firm—Goodman & Teitelbaum

[57] ABSTRACT

A dental attachment for connecting a removable dental prosthesis to an adjoining fixed tooth. The attachment includes a female member and a male assembly. The female member is inserted into the fixed tooth and includes an open mouth channel at the forward face of the fixed tooth. The male assembly includes an insert member which is received within a receiving member. The receiving member includes an elongated housing having an upwardly extending face plate through which a chamber is formed into the elongated housing to receive the insert member. The insert member includes an elongated shank portion with an upright plug at its forward end. Rearward of the plug is provided a stabilizing projection. The face plate is sandwiched between the stabilizing projection and the forward plug to provide additional stability. The male member is disposed in the dental prosthesis with the plug portion projecting forward of the face of th eprosthesis. The plug is sidably received within the channel in the female member. The upright plug can have bifurcated sections which are spread apart by a tapered plug to adjustably control the tension between the male assembly and the female member. The insert member can inclue two opposing half sections with a spring member disposed between the half sections.

18 Claims, 3 Drawing Sheets

STABILIZED DENTURE ATTACHMENT

BACKGROUND OF THE INVENTION

This invention relates to dental attachments, and more particularly to a stabilized dental attachment for attaching a removable dental prosthesis to an adjoining fixed tooth.

As a result of broken or missing dentition, a dental prosthesis is often provided in the mouth of a patient. The prosthesis, such as a denture, must be securely retained in place between existing fixed dentition. Yet, it should be easily removable for cleaning, fixing, repair and replacement.

Numerous types of dental attachments are available for coupling the prostheses to the fixed dentition. Most of these permit removable connection. Each patient, however, requires a different amount of tightness between the prosthesis and the fixed dentition. Since the sensitivity level of each patient varies, too tight a fit may be disturbing to one patient while it may be comfortable to another patient. Most of the dental attachments, however, have a predetermined fixed amount of frictional engagement between the detachable parts, and varied adjustment is not feasible.

Additionally, after continued usage and removal of the prosthesis, the frictional engagement between the removable parts tends to wear and the denture becomes loose. Here again, appropriate adjustment would be desirable to increase the frictional engagement after continued usage.

U.S. Pat. No. 4,196,516 describes an attachment for a denture having a female housing which is embedded in the fixed dentition, and a male assembly which is embedded in the removable denture. An appropriate adjustment screw is provided on the male assembly which permits increasing or decreasing the frictional engagement between the male and female portions to satisfy particular needs of a patient as well as to enhance the frictional engagement after continued usage.

While the aforementioned denture attachment has been most innovative and useful, there can result slight instability between the portions forming the male assembly. Specifically, some axial rotation can be introduced between the male members as a result of continued use. Additionally, the adjustability of the male member can cause breakage of the teeth under specific conditions. Also, the use of the adjustment screw is inconvenient and can loosen to cause slippage of the parts of the attachment.

Accordingly, while the aforementioned device has been found useful, further improvements in such dental attachment would be warranted.

SUMMARY OF THE INVENTION

An object of the present invnetion is to provide a dental attachment for connecting a removable dental prosthesis to an adjoining fixed tooth which avoids the aforementioned problems of the prior art devices.

Another object of the present invention is to provide a dental attachment for connecting a denture to a fixed tooth which provides improved stability, avoids rotation of the parts, and provides a greater assurance against breakage of the teeth.

A further object of the present invention is to provide a stabilized dental attachment for connecting a removable dental prosthesis to a fixed tooth which permits adjustability of the frictional engagement between the various members of the dental attachment without the use of a screw adjustment.

Yet another object of the present invention to provide a dental attachment having a male assembly provided with a stabilizing projecting wall.

Briefly, in accordance with the present invention, there is provided a dental attachment for connecting a removable dental prosthesis to an adjoining fixed tooth. The dental attachment includes a female member in the form of an upright housing having an open mouth channel. The female member is embedded in the fixed tooth with the open mouth exposed and facing the dental prosthesis. A male assembly is provided which includes an insert member extending into a receiving member. The receiving member includes an elongated housing having a face plate that extends upwardly above the height of the elongated housing of the receiving member. A receiving chamber extends through the face plate and continues into the elongated housing. The insert member includes an elongated shank portion which can be inserted into the receiving chamber. At the front end of the elongated shank portion is provided a bifurcated upright plug which is positioned in front of the face plate when the shank portion is inserted in the receiving chamber.

The insert member is secured to the receiving member by means of a clip insertable in aligned apertures laterally formed through the insert and receiving members. The male assembly is embedded into the dental prosthesis with the face plate at the surface of the prosthesis, whereby the bifurcated plug projects from the prosthesis to be slidably inserted into the channel of the female member.

In order to improve the stability of the male assembly, a stabilizing projecting wall extends upward from the shank portion rearwardly spaced from the bifurcated plug. With the insert member extended into the receiving member, the face plate is straddled with the bifurcated plug on one side and the stabilizing wall on the other side to thereby increase the stability of the male assembly by avoiding vertical rotation between the members forming the male assembly, thus strengthening the male assembly in order to prevent possible breakage of the teeth.

The bifurcated plug can be sized to frictionally slide into the channel in the female member. This can be achieved by outwardly flaring apart the bifurcated plug sections. Adjustment of the separation between the plug sections can be achieved by the closing together of the bifurcated plug sections or by spreading them further apart by wedging a tool into the split between the plug sections. Alternately, a tapered hole can be formed as part of the split between the plug sections, and a correspondingly tapered plunger can be inserted into the tapered hole to further spread apart the bifurcated plug sections. Additionally, the insert member can be formed in two parts with a spring disposed between the two parts to continuously force the plug sections apart.

The aforementioned objects, features and advantages of the invention will, in part, be pointed out with particularity, and will, in part, become obvious from the following more detailed description of the invention, taken in conjunction with the accompanying drawing, which forms an integral part thereof.

BRIEF DESCRIPTION OF THE DRAWINGS

In the drawings.

In the various figures of the drawing, like reference characters designate like parts

DESCRIPTION OF THE PREFERRED EMBODIMENTS

Figure 1:
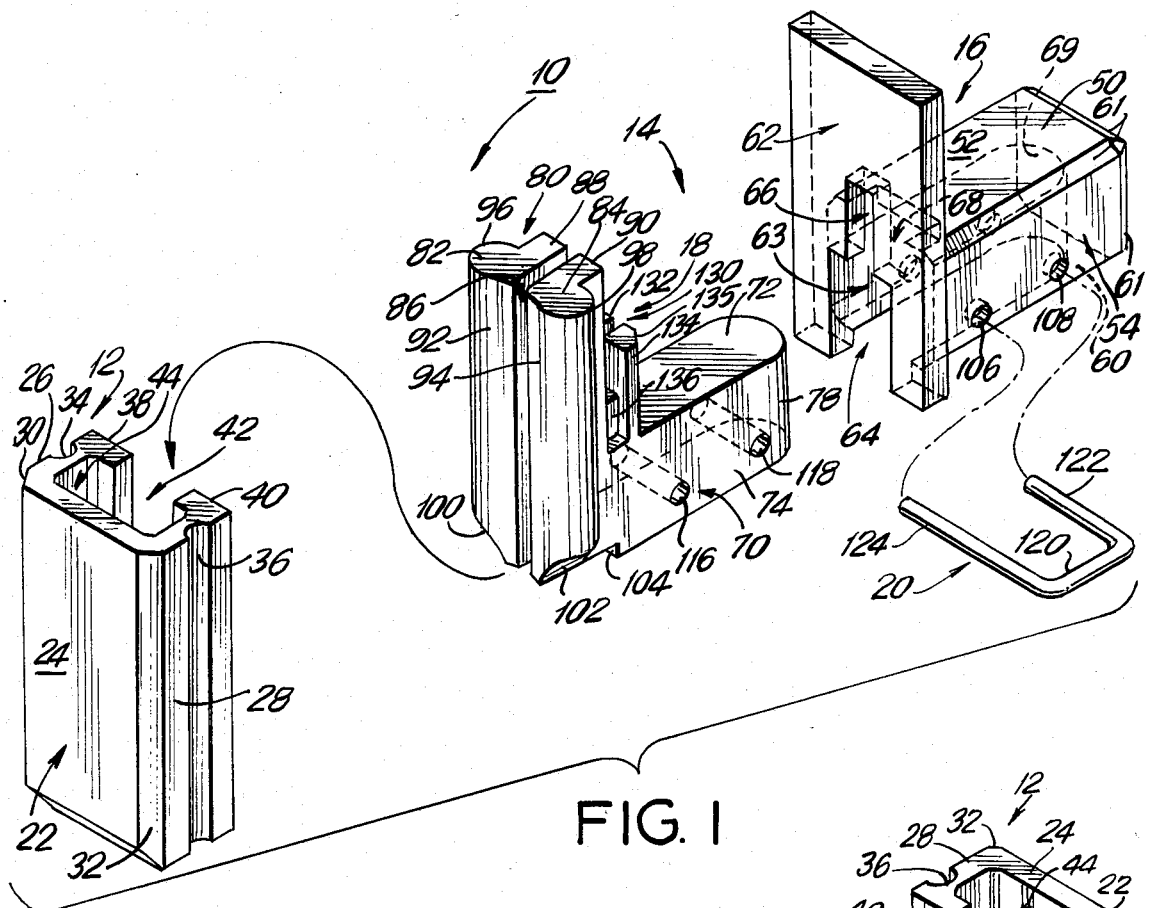
FIG. 1 is an exploded perspective view showing the various parts of the dental attachment prior to their assembly.
Figure 2:
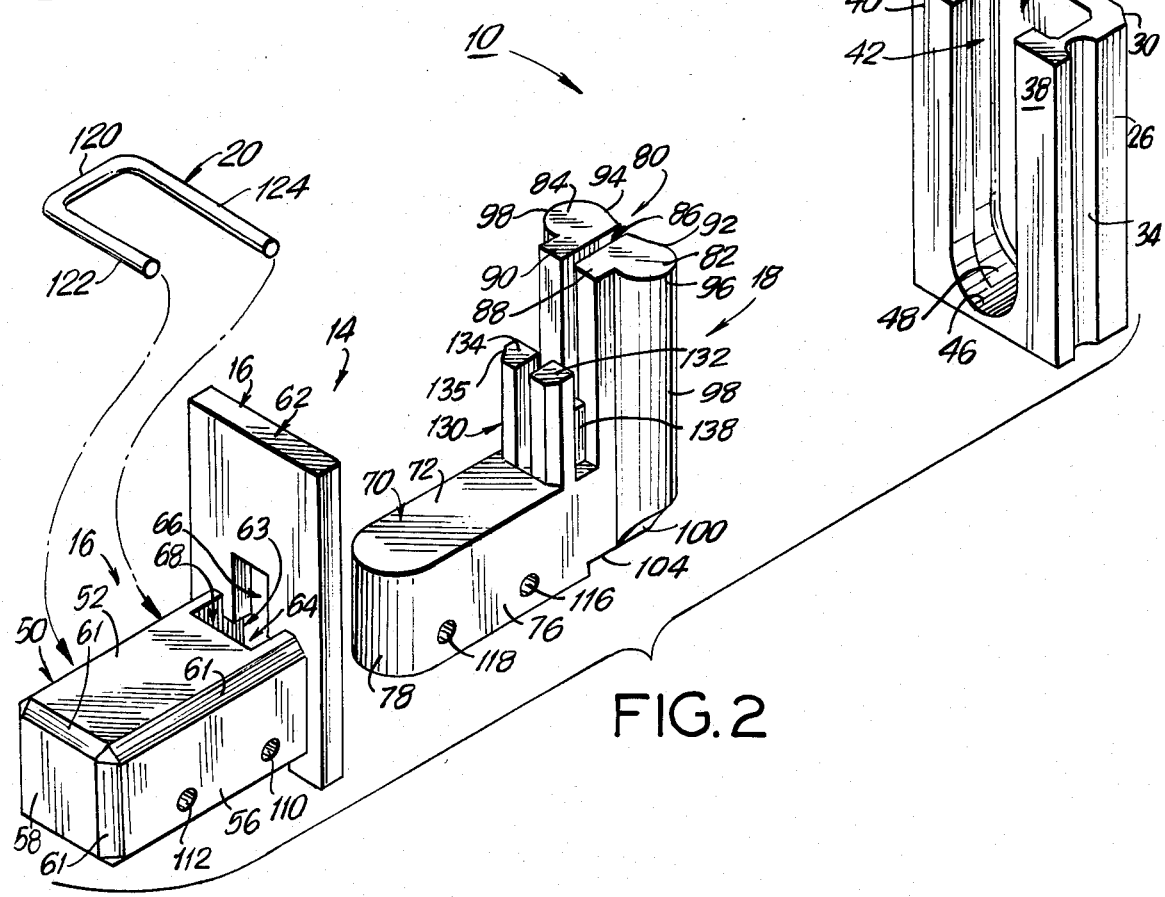
FIG. 2 is an exploded perspective view of the parts shown in FIG. 1, showing the opposite side of the parts.

Referring now to the drawings, and specifically FIGS. 1 and 2, the dental attachment is shown generally at 10, and includes a female member 12 and a male assembly 14, the male assembly 14 including a receiving member 16 and an insert member 18. A pin 20 interconnects the insert member 18 to the receiving member 16.

The female member 12 includes an upright housing 22 in the form of a U-shaped channel. The housing includes a rear wall 24 with a pair of side walls 26, 28. The junctions between the rear wall 24 and the side walls 26, 28 are beveled at 30, 32. Each of the side walls include an arcuate indent 34, 36 to improve the retention of the embedded female member 12 in the fixed dentition. Side walls 26, 28 terminate in opposing inwardly directed confronting front walls 38, 40 which terminate in spaced apart relationship to define therebetween a vertical mouth 42 which provides entry into the internal U-shaped channel 44 in the female housing 22. By means of the open mouth 42, the channel 44 defines a generally T-shaped chamber in cross section.

The lower end of the mouth 42 is closed and includes an arcuately shaped lower wall 46. Likewise, the lower end of the channel 44 is closed and terminates in a lower arcuate wall 48 which mates with the edge 46 at the bottom thereof.

The receiving member 16 of the male assembly 14 has a substantially rectangular housing 50 including an upper wall 52, opposing side walls 54, 56, a rear wall 58 and a bottom wall 60. The upper and end edges are beveled as at 61. At the front of the housing 50 is an upstanding face plate 62 extending laterally outwardly from both sides of housing 50, extending upwardly above the top of the housing 50, and extending downwardly slightly below the bottom of the housing 50. A receiving chamber 63 extends through the face plate 62 forming a lower substantially rectangular opened aperture 64 in the face plate 62. The chamber aperture 64 continues into the interior of the housing 50. The chamber 63 extends upwardly in the face plate 62 to also include an upper notched opening 66 extending from the chamber aperture 64 to above the housing 50. A portion of the upper wall 52 of the housing 50 also includes a notched opening 68 rearward of the face plate in communication with the chamber 63. The chamber aperture 64 has an arcuate rear section 69 and an open bottom.

The insert member 18 includes a solid shank portion 70 having a flat upper wall 72, a pair of opposing side walls 74, 76 and an arcuate rear wall 78. The shape of the shank portion 70 corresponds to the receiving chamber aperture 64 formed in the housing 50.

Integral with the shank portion 70 and supported at the forward end thereof is a bifurcated plug 80 including a pair of opposing winged column sections 82, 82 spaced apart by an intermediate channel 86. The bifurcated plug 80 has a T-shape with a pair of arms 88, 90 extending rearwardly from the laterally extending winged sections 82, 84 at its face. The opposing winged sections 82, 84 include an arcuate front face 92, 94 and rounded exterior side edges 96, 98. The lower end of the winged sections 82, 84 are tapered at 100, 102 so as to define a leading forward end for insertion into the channel 44 in the female housing 12, as will hereinafter be explained. The plug 80 extends upwardly above the height of the shank portion 70. An upwardly directed step 104 is formed at the bottom of the plug 80 to accommodate the walls 46 and 48 at the bottom of the mouth 42 and channel 44 in the female housing 12 when assembled, as can best be seen in FIG. 4.

A pair of apertures 106, 108 are formed in spaced relationship through the side wall 54 and correspondingly aligned apertures 110, 112 are formed in wall 56 of the housing 50 of the receiving member 16. A pair of correspondingly aligned bores 116, 118 are formed into the shank portion 70.

The U-shaped pin 20 includes a bight portion 120 with a pair of leg portions 122, 124, the leg portions 122 being shorter than the leg portion 124. When assembled, the male insert member 18 is inserted into the receiving member 16 and with the holes 106, 110, 116 and 108, 112, 118 aligned, the pin 20 is inserted therethrough. Making one leg portion of the pin 20 longer facilitates the insertion thereof into the aligned holes where the longer leg portion 124 acts as a guide. The U-shaped pin 20 holds the male assembly 14 securely together.

In order to increase the stability of the male assembly 14 and prevent vertical rotation between the receiving member 16 and insert member 18, there is provided, rearward of the bifurcated plug 80, a stabilizing projection 130 including a pair of bifurcated column members 132, 134 having beveled corners 135. The stabilizing projection 130 is spaced rearwardly of the bifurcated plug 80 and is separated by means of bridge portions 136, 138. The bridge portions 136, 138 are raised above the height of the shank portion 70 and recessed inwardly from the side walls 74, 76 of the insert member 18. The projecting stabilizing member 130 can be inserted through the notched opening 68 in the receiving member 16 so that the stabilizing projection 130 is on one side and the bifurcated plug 80 is on the other side of the face plate 62 to straddle the face plate 62 therebetween to thereby stabilize the male assembly 14. The raised notch opening 66 in the face plate 62, will rest on the recessed bridge portions 136, 138. By means of this stabilizing projection, there is also provided a strengthening of the male assembly 14 which is required during the course of adjustment in order to prevent breakage of the teeth.

Figure 3:
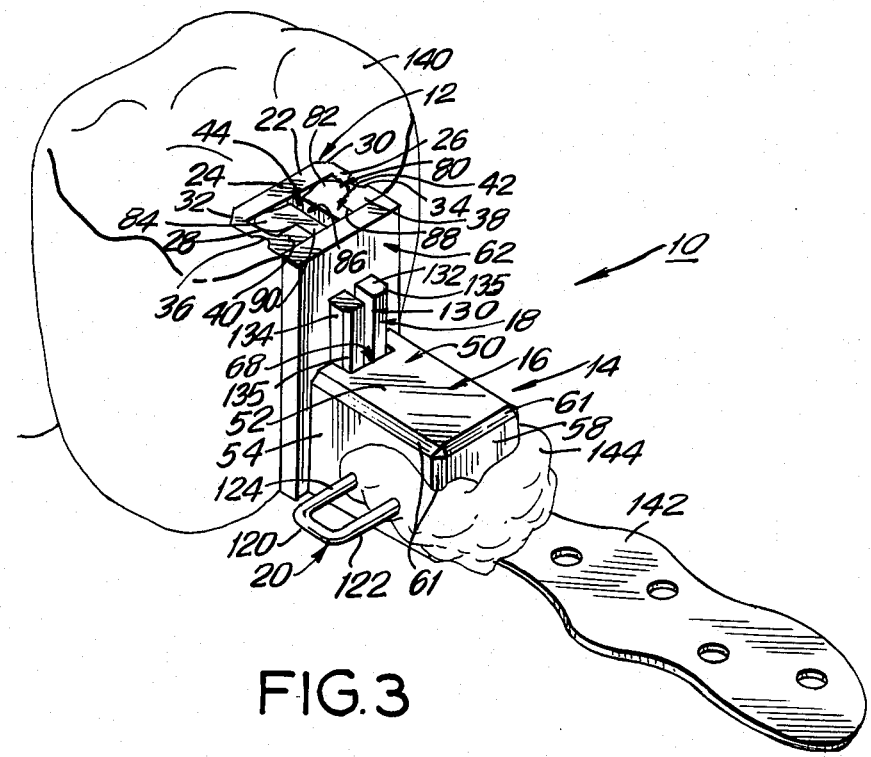
FIG. 3 shows assembled dental attachment connected to a fixed dentition.

Referring to FIG. 3, a typical installation is shown wherein the female portion 12 is embedded within a patient's fixed tooth 140, the mouth 42 of the female portion 12 being open and exteriorly facing. The male assembly 14 is interconnected with the insert member 18 secured within the receiving member 16 by the U-shaped pin 20. A conventional crib 142 for a denture housing is affixed in the usual manner by solder 144, or the like, to the housing 50 of the male assembly 14. The stabilizing projection 130 is shown seated behind the face plate 62 and the bifurcated plug 80 is seated within the female channel 44.

Figure 4:
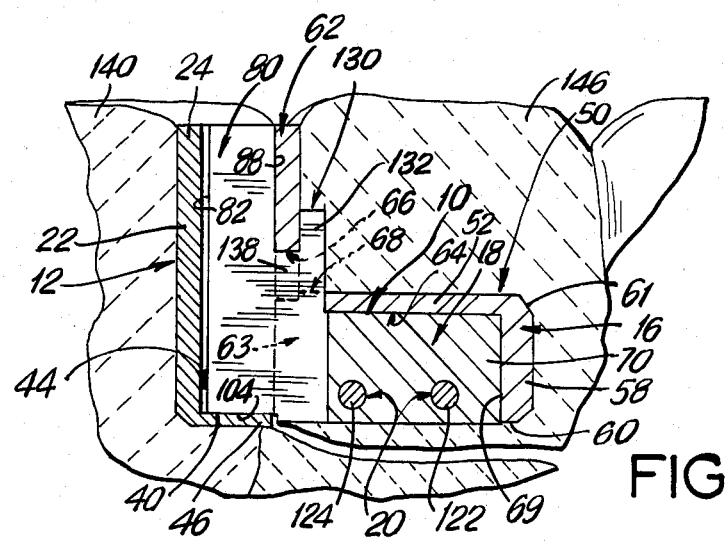
FIG. 4 is an elevational cross sectional view through a finished assembly, showing the interconnection between the denture and the fixed dentition by means of the dental attachment.
Figure 5:
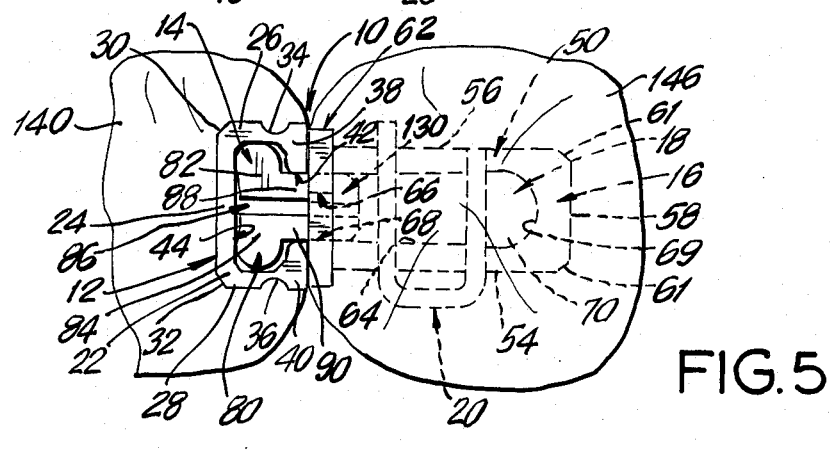
FIG. 5 is a top plan view of the finished assembly shown in FIG. 4.

As shown in FIGS. 4 and 5, the male assembly 14 is embedded within a dental prosthesis 146 with the face plate 62 at the surface of the dental prosthesis 146 and the bifurcated plug 80 projecting from the prosthesis 146. The prosthesis 146 is secured by lowering the prosthesis 146 in a position adjacent the fixed dentition 140. The leading lower end 100, 102 of the bifurcated plug 80 will be received in the upper end of the channel 44 and will continue to slide downwardly into the channel 44 until it bottoms into the closed base wall 48 of the channel 44.

As noted in FIGS. 3 and 5, the arcuate curvature 92, 94 at the front of the bifurcated plug 80, and the curved exterior side edges 96, 98 of the wings of the plug 80 provide a tight fit within the channel 44 in the female housing 12. At the same time, it provides adequate spacing for proper movement in accordance with the needs of the patient during chewing and regular usage of the dental prosthesis 146.

It should be noted that there is no adjustment screw required to adjust the bifurcated sections 82, 84 of the plug 80. Generally, the bifurcations 82, 84 are formed just sufficiently spaced apart to provide an adequate frictional fit within the channel 44 of the female member 12. To provide additional frictional engagement, if required, the plug sections 82, 84 can be formed slightly flared apart. Upon insertion into the channel 44, the flared section 82, 84 are forced toward each other to provide a tight fit within the channel 44. Furthermore, any looser adjustment that is needed, can be achieved by squeezing the bifurcated sections 82, 84 together to loosen the fit within the channel 144. Alternately, by inserting a tool between the bifurcated sections 82, 84 and wedging them apart, the frictional engagement within the channel 44 can be increased. These adjustments by wedging apart or squeezing together of the bifurcated sections can be done by the dentist or technician in situ, as the patient's prosthesis is fitted onto the fixed dentition 140.

Figure 6:
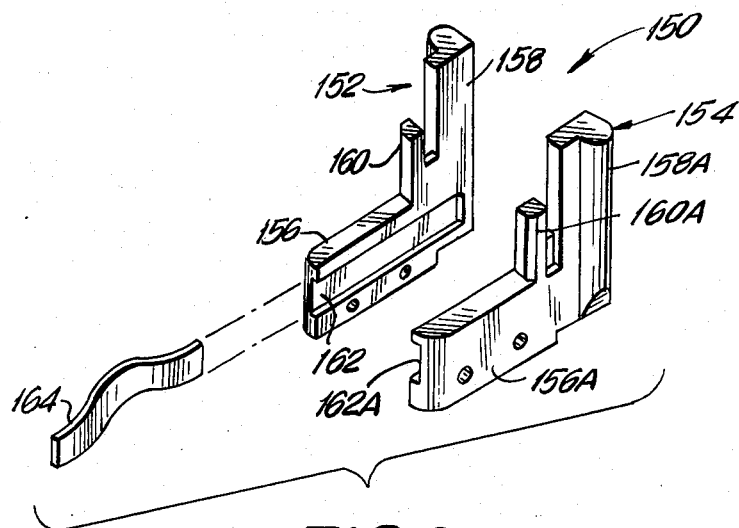
FIG. 6 is an exploded perspective view of another embodiment of the insert member of the male assembly, showing a spring to separate the parts of the insert member.

FIG. 6 shows an alternate type of insert member 150 which can provide a continuous spreading apart of the bifurcated sections in order to enhance the frictional engagement and increase the tension between the male and female members. The insert member 150 is formed of two sections 152, 154 as the left and right hand portions of the insert member 150. The structure is substantially similar to that previously shown only is now split into mating sections 152, 154. Each of the sections 152, 154 includes a shank portion 156, 156A, a plug portion 158, 158A and a stabilizing member 160, 160A. Internally of each section 152, 154, there is provided mating portions of an elongated channel 162, 162A.

An S-shaped leaf spring 164, having a width which can be received within the composite mating portions of the channel 162, 162A, is sandwiched between the two half sections 152, 154. The spring 164 spreads the two sections apart. When the two sections are mated with the spring 164 therein, they compositely form the male insert member 150 which is inserted into the male receiving member 16 shown in FIG. 1, where the receiving member 16 holds the insert member 150 together. The spring 164 extends far enough forward to spread apart the plug portions 158, 158A. This provides a tension for an adequate frictional engagement upon insertion of the plug portions 158, 158A into the female channel 44.

Figure 7:
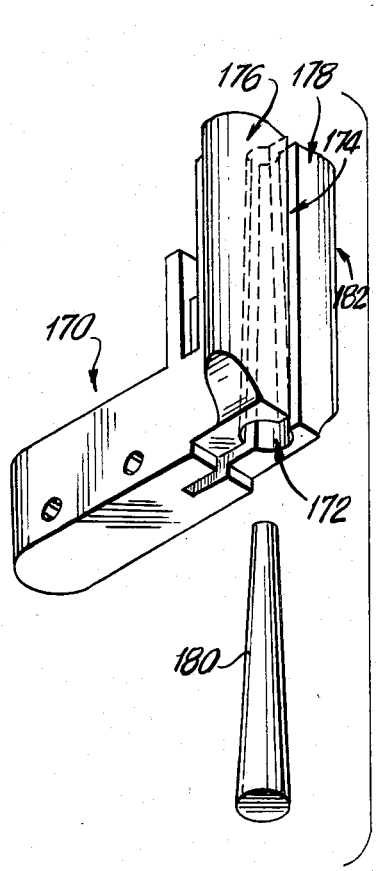
FIG. 7 is an exploded perspective view of yet a further embodiment of the insert member of the male assembly, showing a tapered hole in the insert member with a correspondingly tapered plunger for insertion therein.

FIG. 7 shows yet a further approach to spreading apart the bifurcated sections in order to provide for adjustment of the tension of the engagement within the female channel 44. The male insert member 170 is substantially similar to that shown in FIG. 1, but includes a tapered bore 172 formed along the bifurcation slot 174 between the opposing bifurcated sections 176, 178. Preferably, the bore 172 is larger at the bottom of the insert member 170, and smaller at the top of the sections 176, 178. A tapered plug or pin 180 can be received in the tapered hole 72. As the plug 180 is inserted, smaller end first, into the bottom of the tapered hole 172, it spreads apart the bifurcated sections 176, 178 in order to adjustably control the tension when the sections 176, 178 are inserted into the female channel 44, where the plug 180 remains in the insert member 170.

Figure 8:
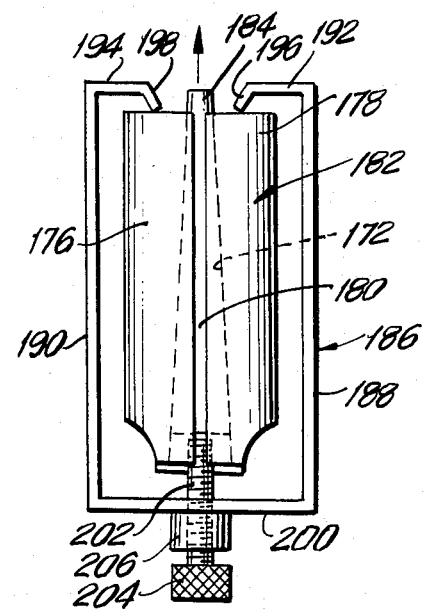
FIG. 8 is an elevational view showing a clamping tool inserting the tapered plunger into the tapered hole of the insert member shown in FIG. 7.

As shown in FIG. 8, the length of the plug 180 substantially corresponds to the height of the bifurcated plug 182 of the insert member 170. Increased tension is provided by pushing the plug 180 further upwardly in the hole 172 to force the sections 176, 178 apart, where the upper end 184 of the plug 180 will project above the top of the bifurcated plug 182.

A clamping tool 186 can be utilized for pushing upward on the plug 180. The clamping tool 186 includes a pair of side arms 188, 190 having top sections 192, 194 with downwardly inclined projecting fingers 196, 198 engaging the tops of the bifurcated sections 176, 178. Through the bottom 200 of the tool 186, a screw 202 is threaded by means of a knurled knob 204. The screw 202 is passed through a fixed internally threaded boss 206 mounted on the tool bottom 200. As the knurled knob 204 is rotated, the upper end of the screw 202 pushes upwardly on the plug 180 so that the plug 180 is forced to move upwardly in the tapered hole 172 to thus spread apart the bifurcated sections 176, 178 to the desired degree required to produce the proper tension within the female channel 44.

After proper adjustment of the tension, the upper portion 184 of the plug 180 projecting above the top of the bifurcated plug 182, can be cut off. It is noted, that in order to reduce the tension, the plug 180 can be pushed back downwardly a desired amount into the tapered hole 172, by using a suitable tool, to allow the bifurcated sections 176 178 to move closer together as permitted by the plug 180.

It should therefore be appreciated, that the present invention provides adjustability of the tension even without the need of a screw adjustment. Furthermore, by providing the stabilizing member behind the face plate 62, the male assembly 14 is more stable and prevents the possibility of any fracture of the patient's teeth or of the dental prosthesis.

There has been disclosed heretofore the best embodiments of the invention presently contemplated. However, it is to be understood that various changes and modifications may be made thereto without departing from the spirit of the present invention.

What is claimed is:

1. A dental attachment for connecting a removable dental prosthesis to an adjoining fixed tooth, comprising:
    a female member including an upright housing having an open mouth channel, said female member being embedded into the fixed tooth with said channel exposed and facing the dental prosthesis;
    a male assembly including an insert member and a receiving member;
    said receiving member including an elongated housing having an upwardly extending face plate, a receiving chamber extending through said face plate and into said elongated housing;
    said insert member including an elongated shank portion insertable into said receiving chamber, said shank portion supporting an upright plug at its forward end for positioning forward of said face plate;
    coupling means for securing said insert member in said receiving member;
    said male assembly being embedded into the dental prosthesis with said face plate at an outer surface of the dental prosthesis and with said plug projecting from the dental prosthesis for slidable insertion into said channel; and
    a stabilizing projection on said shank portion spaced rearward of said plug, wherein said face plate is straddled by said plug an said stabilizing projection for increased stability of said male assembly.

2. A dental attachment as in claim 1, wherein a top wall of said elongated housing of said receiving member is notched rearward of said face plate for communication with said receiving chamber to accommodate said stabilizing projection.

3. A dental attachment as in claim 1, wherein a bridge portion is provided in the space between said face plate and said stabilizing projection, and wherein an opening is provided in said face plate extending upwardly from said receiving chamber to receive said bridge portion therein.

4. A dental attachment as in claim 1, wherein said plug and stabilizing projection are bifurcated to provide pairs of adjacent column sections.

5. A dental attachment as in claim 1, wherein a lower end of said channel is closed and arcuately shaped.

6. A dental attachment as in claim 5, wherein a bottom of said plug is upwardly stepped from a bottom of said shank portion to accommodate said closed lower end of said channel when said plug is inserted into said channel.

7. A dental attachment as in claim 1, wherein a rear of said shank portion is arcuate for insertion into said receiving chamber.

8. A dental attachment as in claim 7, wherein a closed end of said receiving chamber is arcuate in shape to conform to said arcuate rear of said shank portion.

9. A dental attachment as in claim 1, wherein said receiving chamber is open at its bottom to accommodate upward insertion of said shank portion into said receiving chamber.

10. A dental attachment as in claim 1, wherein said coupling means includes pairs of aligned holes provided into said elongated housing and the shank portion, and a U-shaped pin insertable into said aligned holes.

11. A dental attachment as in claim 10, wherein one leg of said U-shaped pin is longer than the other leg to facilitate insertion into said aligned holes.

12. A dental attachment as in claim 1, wherein said insert member includes two opposing half sections, an elongated channel section provided along said elongated shank portion of each half section with said channel section extending into said upright plug of each half section, said channel sections providing a composite channel between said half sections, and a spring member received in said composite channel for spreading apart said half sections to provide adequate tension for said upright plug of each half section within said female member channel.

13. A dental attachment as in claim 1, including means for adjusting said plug to control frictional retention between said plug and walls of said channel.

14. A dental attachment as in claim 13, wherein said adjusting means includes a tapered hole provided along a bifurcation in said plug, and a tapered plug insertable into said tapered hole for spreading apart bifurcated sections of said plug to increase tension upon insertion of said plug into said channel in said female member.

15. A dental attachment as in claim 14, and further comprising an insertion tool for upwardly inserting said tapered plug into said tapered hole to spread apart said bifurcated sections.

16. A dental attachment for connecting a removable dental prosthesis to an adjoining fixed tooth, comprising:
    a female member including an upright housing having an open mouth channel, said female member being embedded into the fixed tooth with said channel exposed and facing the dental prosthesis;
    a male assembly including an insert member and a receiving member;
    said receiving member including an elongated housing having an upwardly extending face plate, a receiving chamber extending through said face plate and into said elongated housing;
    said insert member including an elongated shank portion insertable into said receiving chamber, said shank portion supporting an upright plug at its forward end for positioning forward of said face plate;
    coupling means for securing said insert member in said receiving member;
    said male assembly being embedded into the dental prosthesis with said face plate at an outer surface of the dental prosthesis and with said plug projecting from the dental prosthesis for slidable insertion into said channel;
    said insert member including two opposing half sections, an elongated channel section provided along said elongated shank portion of each half section with said channel section extending into said upright plug of each half section, said channel sections providing a composite channel between said half sections, and a spring member received in said composite channel for spreading apart said half section to provide adequate tension for said upright plug of each half section within said female member channel; and
    a stabilizing projection being provided on said shank portion of each half section spaced rearward of said plug on each half section, said face plate being straddled by said plug and said stabilizing projection on each half section for increased stability of said male assembly.

17. A dental attachment for connecting a removable dental prosthesis to an adjoining fixed tooth, comprising:
- a female member including an upright housing having an open mouth channel, said female member being embedded into the fixed tooth with said channel exposed and facing the dental prosthesis;
- a male assembly including an insert member and a receiving member;
- said receiving member including an elongated housing having an upwardly extending face plate, a receiving chamber extending through said face plate and into said elongated housing;
- said insert member including an elongated shank portion insertable into said receiving chamber, said shank portion supporting an upright plug at its forward end for positioning forward of said face plate;
- coupling means for securing said insert member in said receiving member;
- said male assembly being embedded into the dental prosthesis with said face plate at an outer surface of the dental prosthesis and with said plug projecting from the dental prosthesis for slidable insertion into said channel;
- means for adjusting said plug to control frictional retention between said plug and walls of said channel, said adjusting means including a tapered hole provided along a bifurcation in said plug, and a tapered plug insertable into said tapered hole for spreading apart bifurcated sections of said plug to increase tension upon insertion of said plug into said channel in said female members; and
- a stabilizing projection being provided on said shank portion spaced rearward of said plug, said face plate being straddled by said plug and said stabilizing projection for increased stability of said male assembly.

18. A dental attachment as in claim 17, and further comprising an insertion tool for upwardly inserting said tapered plug into said tapered hole to spread apart said bifurcated sections.

* * * * *